United States Patent [19]

Braatz et al.

[11] Patent Number: 5,403,750
[45] Date of Patent: Apr. 4, 1995

[54] BIOCOMPATIBLE, LOW PROTEIN ADSORPTION AFFINITY MATRIX

[75] Inventors: James A. Braatz, Beltsville; Aaron H. Heifetz, Columbia, both of Md.

[73] Assignee: W. R. Grace & Co.-Conn., New York, N.Y.

[21] Appl. No.: 682,502

[22] Filed: Apr. 8, 1991

Related U.S. Application Data

[63] Continuation-in-part of Ser. No. 665,498, Mar. 6, 1991, Pat. No. 5,169,720.

[51] Int. Cl.$^6$ ............................................. G01N 33/545
[52] U.S. Cl. ................................... 436/531; 528/48; 528/52; 528/53; 528/59; 528/904; 427/2.13; 427/207.1; 427/221; 427/435; 210/500.24; 428/423.1; 428/423.9; 428/424.2; 428/424.6; 428/425.1; 428/425.5; 428/425.6; 604/8; 604/19; 604/403; 435/174; 435/176; 435/181; 435/182; 525/403; 525/418; 525/420; 525/424; 525/454; 436/120; 436/129; 436/131
[58] Field of Search ............................ 528/48, 52, 53, 59, 528/904; 427/2, 207.1, 221, 435; 210/500.24; 428/423.1, 423.9, 424.2, 424.6, 425.1, 425.5, 425.6; 604/8, 19, 403; 435/174, 176, 181, 182; 525/403, 418, 420, 424, 454; 436/531, 120, 128, 131

[56] References Cited

U.S. PATENT DOCUMENTS

| | | | |
|---|---|---|---|
| 3,905,923 | 9/1975 | Klug | 435/182 |
| 3,939,123 | 2/1976 | Matthews et al. | 528/60 |
| 4,094,744 | 6/1978 | Hartdegen et al. | 435/182 |
| 4,177,038 | 12/1979 | Biebricher et al. | 8/192 |
| 4,182,827 | 1/1980 | Jones et al. | 528/60 |
| 4,226,935 | 10/1980 | Fusee | 435/14 |
| 4,241,537 | 12/1980 | Wood | 47/77 |
| 4,266,030 | 5/1981 | Tschang et al. | 435/180 |
| 4,371,611 | 2/1983 | Fusee | 435/14 |
| 4,412,000 | 10/1983 | Lehamnn et al. | 435/179 |
| 4,439,585 | 3/1984 | Gould et al. | 525/127 |
| 4,485,227 | 11/1984 | Fox | 528/61 |
| 4,569,981 | 2/1986 | Wenzel et al. | 528/67 |
| 4,681,851 | 7/1987 | Baumgarten et al. | 435/262 |
| 4,794,090 | 12/1988 | Parham et al. | 436/531 |
| 4,885,250 | 12/1989 | Eveleigh et al. | 435/181 |
| 4,940,737 | 7/1990 | Braatz et al. | 521/103 |

*Primary Examiner*—Samuel A. Acquah
*Attorney, Agent, or Firm*—Beverly K. Johnson

[57] ABSTRACT

Affinity matrices useful for the chromatography and immobilization of biological materials and the method of preparing and using the same are disclosed. The affinity supports are based on hydrated polyurethane polymers which have been activated to provide a means for covalently attaching a variety of bioaffinity agents. The hydrated polymer matrices are characterized by their biocompatibility and resistance to nonspecific protein adsorption. Preferably, the prepolymers used to prepare the hydrated polymers are isocyanate-capped oxyethylene-based diols or polyols, at least 75% of said diols and polyols having a molecular weight of 7000 to about 30,000.

25 Claims, No Drawings

BIOCOMPATIBLE, LOW PROTEIN ADSORPTION AFFINITY MATRIX

This application is a continuation-in-part of U.S. patent application Ser. No. 665,498, filed Mar. 6, 1991, now U.S. Pat. No. 5,169,720.

BACKGROUND OF THE INVENTION

This invention relates to matrices for use in affinity chromatography and in the immobilization of biologically active materials. More specifically, this invention relates to affinity supports based on a unique series of hydrated polyurea-polyurethane polymers which have been activated to provide a means for immobilizing and chromatographing a wide variety of bioaffinity agents.

Bioaffinity separations generally involve at least one biomacromolecule, such as a protein or nucleic acid, as one of the components of the binding pair. Examples of such bioaffinity binding pairs include: antigen-antibody, substrate-enzyme, effector-enzyme, inhibitor-enzyme, complementary nucleic acid strands, binding protein-vitamin, binding protein-nucleic acid; reactive dye-protein, reactive dye-nucleic acid; and others. The terms ligand and binder will be used to represent the two bioaffinity agents in specific binding pairs. By "ligand" is meant an antigen, hapten, nucleic acid, vitamin, dye or small organic molecule including enzyme substrates, effectors, and inhibitors and the like. By binder is meant an antibody, enzyme, nucleic acid, binding protein, synthetic mimics of binding proteins such as polylysine and polyethyleneimines or other macromolecules capable of specific binding, enzyme/substrate interactions, etc. . . .

The affinity supports of the invention are based on activated polymers prepared from high molecular weight isocyanate end-capped prepolymers which are substantially comprised of ethylene oxide units. Activation of the polymers is accomplished by first derivatizing the prepolymer with a reactive compound having an NCO-reactive group and a second functional group. The derivatized or modified prepolymers are polymerized with water to yield a modified polyurea-urethane polymer characterized by the second functional group inserted into the prepolymer. The modified polyurea-urethane polymer is then activated by contacting the polymer with an activating compound to convert said second functional group to an active species which is capable of selectively covalently bonding a specific ligand or binder of interest.

Numerous polyurethane polymers have been previously identified, among them both foamed and non-foamed materials. Of the nonfoamed materials, quite a few hydrogel polymers, prepared from various prepolymers, have been prepared and used for widely varying applications. Typically, hydrogels are formed by polymerizing a hydrophilic monomer in an aqueous solution under conditions such that the prepolymer becomes crosslinked, forming a three-dimensional polymeric network which gels the solution. Polyurethane hydrogels are formed by polymerization of isocyanate-end capped prepolymers to create urea and urethane linkages.

Representative examples of previously disclosed polyurethane hydrogels include the following: U.S. Pat. No. 4,241,537 (Wood) discloses a plant growth media comprising a hydrophilic polyurethane gel composition prepared from chain-extended polyols; random copolymerization is preferred with up to 50% propylene oxide units so that the prepolymer will be a liquid at room temperature. U.S. Pat. No. 3,939,123 (Matthews) discloses lightly crosslinked polyurethane polymers of isocyanate terminated prepolymers comprised of poly-(ethyleneoxy) glycols with up to 35% of a poly(propyleneoxy) glycol or a poly(butyleneoxy) glycol. In producing the Matthews polymer, an organic polyamine is used as a crosslinking agent. The Matthews prepolymers form a cross-linked, three dimensional structure when polymerized as taught in the patent. U.S. Pat. No. 4,182,827 (Jones) discloses a similar use of polyamines in the formation of polyurethane hydrogels.

Several types of compounds have been reacted with prepolymers or with matrix bases to act as spacing or coupling compounds in the attachment or immobilization of biologically active agents. For example, U.S. Pat. No. 4,226,935 (Fusee) discloses reacting an amino acid and/or a protein with an excess of a urethane prepolymer, curing the resulting product to form a polymer matrix, and coupling an enzyme thereto by use of a carbodiimide. U.S. Pat. No. 4,177,038 (Biebricher et al.) teaches the use of spacers which may be diamines, amino-alcohols or diols.

Modified polyurethane polymers also have been prepared. U.S. Pat. No. 4,439,585 (Gould et al.) teaches a polyurethane diacrylate composition obtained by reacting a diacrylate in the presence of a hydrophilic polyurethane resin. U.S. Pat. No. 4,485,227 (Fox) discloses a poly-(ether-urethane-urea) prepared by condensations of a prepolymer with primary diamines, then with an amine-reacting agent. U.S. Pat. No. 4,569,981 (Wenzel et al.) discloses water-dispersible plastics precursors based on isocyanate-terminated prepolymers which have been hydrophilically modified with ionic groups and/or ethylene oxide groups.

Biocompatibility is an increasingly desirable characteristic for polymeric hydrogels and hydrated polymers, which would find numerous uses in the health care field if the appropriate properties can be obtained. However, many conventional hydrogels and polymers are not taught to be biocompatible. In addition, modification of a polymer surface frequently results in increased nonspecific binding of unwanted proteins. Because affinity separation is a powerful technique used in laboratory and health care to purify various biologically active materials, there exists a need for affinity matrices which have improved biocompatibility and increased resistance to nonspecific protein adsorption.

SUMMARY OF THE INVENTION

A new class of hydrophilic polyurethane prepolymers and related crosslinked hydrated polymers has been found for use in the preparation of affinity matrices which are uniquely characterized by biocompatibility and resistance to nonspecific protein adsorption. The matrices are comprised of the hydrated polymer, or a support coated or impregnated with the hydrated polymer, which polymer has been activated to provide specific reactivity to a ligand or binder molecule of interest. The hydrated polymer is preferably derived from polymeric monomer units (the prepolymer units) at least 75% of which are oxyethylene-based diols or polyols having number average molecular weights of about 7000 to about 30,000, with essentially all of the hydroxyl groups of these diols or polyols capped with polyisocyanate. The prepolymers useful in this invention are prepared by reacting the selected diols or polyols with polyisocyanate at an isocyanate-to-hydroxyl ratio of about 1.8 to about 2.2 so that essentially all of the hydroxyl groups of the polyols are capped with polyisocyanate. Polymerization to gel the prepolymer solution may be accomplished by contact with water to yield a polyurea-urethane polymer or with another crosslinking agent to yield a polyurethane polymer.

The polyurethane polymer system of this invention provides modified prepolymers and polymers having highly desirable properties which make them particularly well suited for use in the field of affinity separations. The hydrated polymers may take the form of water-swellable, three-dimensional hydrogels. Alternatively, they may take the form of a dense or thin coating or impregnant on a substrate, including, under dilute conditions, a monomolecular or substantially monomolecular layer. The coatings and impregnates of this invention are considered gels or hydrogels and are included by those terms unless otherwise noted. The terms gel or hydrogel are meant to refer to polymers which are non-foamed in structure.

It is a primary object of the present invention to provide affinity matrices which are characterized by biocompatability and a unique surface which resists nonspecific protein adsorption. It is a related object to provide polymer-based affinity matrices which are capable of modification and yet retain a marked resistance to nonspecific adsorption or binding of protein.

It is a further object of the present invention to provide hydrophilic, biocompatible polymers suited for the preparation of affinity support matrices.

DETAILED DESCRIPTION OF THE INVENTION

The affinity support of the invention is prepared from activated hydrophilic polyurethane or polyurea-urethane polymers which are uniquely characterized by specific reactivity due to the addition of specific functional groups to the polymer molecule. The prepolymers from which the activated polymer compounds are prepared are polymeric monomer units which are oxyethylene-based alcohols which include monofunctional alcohols, diols and polyols with essentially all of the hydroxyl groups capped with polyisocyanate. The prepolymer is modified or derivatized by reaction with a compound having a first functional group which is NCO-reactive. The terms "modified" and "derivatized" will be used interchangeably herein. The modifying compound also has a second functional group which is non-reactive with the NCO groups of the prepolymer or is less reactive, preferably substantially less reactive, with the NCOs than the NCO-reactive group (that is, than the first functional group). The NCO—reactive group may be a sulfhydryl (—SH), amino (—NH$_2$), hydroxyl (—OH) or carboxyl (—COOH) group.

Polymerization of partially modified prepolymers in water or an aqueous solution acts to gel the solution or a deposited layer of the composition to form a modified polyurethane or polyurea-urethane polymer. The modified polymer is characterized by the second functional group which was inserted in the prepolymer molecule. To activate the modified polymer, the polymer is reacted through said second functional group with an activating compound. The activating compound has a functional group which is reactive with said second functional group of the polymer and a nonreactive group which is less reactive, or substantially less reactive, with said second functional group but which is capable of selectively binding by covalent bond to a specific biological ligand or binder.

Prepolymer Preparation

The prepolymers utilized to prepare the affinity matrices of this invention are formed from oxyalkylene-based alcohols. These can be monofunctional alcohols or they can be diols or polyols, including diols or polyols made up of ethylene oxide monomer units. The proportion of ethylene oxide units may vary, and is described in more detail below. Prepolymers are formed when diols and/or polyols are end-capped with di- or polyfunctional isocyanates as described below. In certain embodiments (i.e., where polymerization is not required), monofunctional alcohols may be end-capped with di- or polyfunctional isocyanates for use in this invention. These compounds are not, strictly speaking, "prepolymers." However, since they are prepared and used in an analogous manner, the term "prepolymer" as used herein will refer to isocyanate-capped monofunctional alcohols as well as diols or polyols.

One extensive class of hydrophilic, isocyanate-capped urethane prepolymer is described in U.S. Pat. No. 4,137,200 (Wood et al.), the teachings of which are incorporated herein. The Wood et al. prepolymers are blends of a monomeric polyol and polyoxyalkylene glycol, the hydroxyl groups of the blend being capped with a polyisocyanate. The polyoxethylene polyol may have a weight average molecular weight of about 100 to about 20,000, and preferably between about 600 to about 6000, with a hydroxyl functionality of about 2 or greater, preferably from about 2 to about 8. The polyols should desirably have about 40 to about 100 mole percent ethylene oxide content.

It is possible, and may be desirable, to incorporate various amounts of a relatively hydrophobic comonomer. Thus, comonomers such as propylene oxide or butylene oxide may be copolymerized as a random copolymer, block-copolymer, or both. Aliphatic, aromatic or aliphatic-aromatic isocyanates may be used, such as those listed hereinbelow. Optionally, a crosslinking agent may be included.

One group of isocyanate-capped urethane prepolymers of this class that can be used in the invention comprises the isocyanate-capped polyesters. Such prepolymers may be made by condensing a polyhydric alcohol with a polycarboxylic acid to form a linear polyester which is then reacted with a slight molar excess of a polyisocyanate to provide an essentially linear polyurethane having terminal isocyanate groups and having an average molecular weight within the range 100 to 20,000, preferably between about 600 to about 6000. Polyhydric alcohols that can be used in preparing such prepolymers include the polyalkylene glycols such as ethylene, propylene and butylene glycol and polymethylene glycols such as tetramethylene and hexamethylene glycols. Another group of isocyanate capped urethane prepolymers that can be used in the invention comprise the isocyanate capped polyethers. These prepolymers can be made by reacting, for example, polyalkylene glycols with diisocyanates of the type listed below to provide a polyurethane having terminal isocyanate groups and having an average molecular weight within the range 100 to 20,000, preferably between about 600 to about 6000. As specific examples of these prepolymers, the HYPOL ® polyurethane prepolymer series available from Grace Specialty Chemicals Co., W. R. Grace & Co.-Conn., is suitable.

A second class of prepolymers suitable for use in this invention comprises polyoxyalkylene diols or polyols which are of generally higher molecular weights and which are predominantly or exclusively made up of ethylene oxide monomer units. This second class is somewhat more preferred for use in this invention. Preferably, at least 75% of the monomer units should be ethylene oxide, more preferably at least 90% and most preferably at least 95% up to about 100%. As specific examples of this class of prepolymers, prepolymers from the BIOPOL® polyurethane prepolymer series available from Grace Specialty Chemicals Co., W. R. Grace & Co.-Conn., will be particularly suitable. These prepolymers will form hydrogels when partially modified as described below.

High molecular weight ethylene oxide-based diols and polyols are used to prepare this second class of prepolymers, derivatized prepolymers and hydrated polymers of the present invention. The diol or polyol molecular weight prior to capping with polyisocyanate preferably should be at least about 7000 to 8000 MW, more preferably about 10,000 to about 30,000 MW. It is preferred to use trihydroxy compounds (triols) in the preparation of the polyols which are the precursors to the prepolymers, derivatized prepolymers and hydrated polymers of this invention. For example, glycerol is a preferred triol. Trimethylolpropane (TMOP), trimethylolethane and triethanolamine are other suitable triols. In addition, tetrols, such as pentaerythritol, may be used to prepare polyols for use in this invention. Triol- or tetrol-based polyols are capped with difunctional or polyfunctional isocyanate compounds as described below to form the prepolymer.

Alternatively, diols of appropriate molecular weight may be used as precursors to the prepolymers of this invention. Diols of appropriate molecular weight are capped with polyfunctional isocyanates as described below to form the prepolymers. High molecular weight polyethylene glycols are particularly useful. Especially desirable in this embodiment are polyethylene glycols of the formula $H(OCH_2CH_2)_xOH$ where x is an average number such that the glycol has an average molecular weight of at least about 7000, preferably about 10,000 to about 30,000. Alternatively, diols may be capped with diisocyanates and used in conjunction with crosslinking compounds to form the hydrated polymers described herein. Crosslinking compounds useful for this purpose include polyfunctional amines and polyfunctional isocyanates. In still another alternative embodiment, diols may be mixed with polyols and the resulting mixture reacted with isocyanates to produce the prepolymer of this invention.

Monofunctional alcohols may be selected as the basic "prepolymer" unit where completely modified prepolymer units are intended. For example, monomethoxy poly(ethylene glycol) can be used. In this embodiment, the monofunctional alcohol is end-capped with polyisocyanate and then modified according to this invention. These modified compounds will not be capable of polymerization. Rather, they will result in small, completely modified prepolymer units which are soluble in water.

The prepolymers of this second class are formed by reacting the hydroxyl groups of the diols or polyols described above with polyisocyanates. "Polyisocyanate" as used herein is intended to refer to both diisocyanates and polyisocyanates, as appropriate, except as indicated by specifying the use of difunctional or polyfunctional isocyanates. Isocyanate end-capped (i.e., isocyanate-terminated) prepolymers are formed.

The selected precursor to the prepolymer influences the choice of polyisocyanate in that the prepolymer structure must lend itself to sufficient crosslinking to gel an aqueous prepolymer solution or to form a crosslinked polymeric coating where those properties are desired. In the embodiment in which the precursors to the prepolymers are polyols (that is, triol-based or tetrol-based), difunctional isocyanates are preferred. If desired, polyfunctional isocyanate compounds may also be used with polyols. Mixtures of suitable isocyanates also may be considered.

Where diols are used as the precursors to the prepolymers, they may be reacted with polyfunctional isocyanate compounds to form the prepolymers of this invention. This combination yields prepolymers having sufficient functional groups for crosslinking in the formation of the hydrated polymer. In an alternative embodiment using diols as the precursors to the prepolymers, the diols may be capped with a difunctional isocyanate. In order to achieve sufficient crosslinking in the hydrated polymer prepared from these difunctional prepolymers, they are used in conjunction with a crosslinking compound. The preferred crosslinker is trimethylolpropane ("TMOP"), although others may be used, for example, glycerol, trimethylolethane, pentaerythritol, triethanolamine, polyfunctional amines, polyfunctional isocyanates, and the like.

Aromatic, aliphatic or cycloaliphatic polyisocyanates may be used in any of the above-described embodiments. The use of aliphatic polyisocyanates permits a greater degree of handling and/or shaping since aliphatic isocyanate-capped prepolymers typically require about 20 to 90 minutes to gel to a hydrated polymer state. By contrast, prepolymers capped with aromatic polyisocyanates will gel more rapidly, in about 30 to 60 seconds. In addition, aliphatic polyisocyanates will be preferred when the hydrated polymer is intended to be used in medical applications, because of decreased toxicological considerations. However, hydrated polymers made using aromatic polyisocyanates in the prepolymer are also useful, as well as being suitable for most industrial uses.

Use of aliphatic polyisocyanates in preparation of the prepolymers may further enhance the biocompatibility of the modified polymer product since the potential degradation products of aliphatic polyisocyanates are reported to be significantly less carcinogenic than those of aromatic isocyanates. However, if aromatic polyisocyanates are used, careful washing or other means for removing any unreacted isocyanate and related amine-containing by-products generally will be sufficient to render the modified polymer biocompatible.

Examples of suitable di- and polyfunctional isocyanates are found in the following list:
toluene-2,4-diisocyanate
toluene-2,6-diisocyanate
commercial mixtures of toluene-2,4 and 2,6-diisocyanates
isophorone diisocyanate
ethylene diisocyanate
ethylidene diisocyanate
propylene-1,2-diisocyanate
cyclohexylene-1,2-diisocyanate
cyclohexylene-1,4-diisocyanate
m-phenylene diisocyanate
3,3'-diphenyl-4,4'-biphenylene diisocyanate 4,4'-biphenylene diisocyanate
4,4'-diphenylmethane diisocyanate
3,3'-dichloro-4,4'-biphenylene diisocyanate
1,6-hexamethylene diisocyanate
1,4-tetramethylene diisocyanate
1,10-decamethylene diisocyanate
cumene-2,4-diisocyanate
1,5-napthalene diisocyanate
methylene dicyclohexyl diisocyanate
1,4-cyclohexylene diisocyanate
p-tetramethyl xylylene diisocyanate
p-phenylene diisocyanate
4-methoxy-1,3-phenylene diisocyanate
4-chloro-1,3-phenylene diisocyanate
4-bromo-1,3-phenylene diisocyanate
4-ethoxy-1,3-phenylene diisocyante
2,4-dimethyl-1,3-phenylene diisocyante
5,6-dimethyl-1,3-phenylene diisocyanate
2,4-diisocyanatodiphenylether
4,4'-diisocyanatodiphenylether benzidine diisocyanate
4,6-dimethyl-1,3-phenylene diisocyanate
9,10-anthracene diisocyanate
4,4'-diisocyanatodibenzyl
3,3'-dimethyl-4,4'-diisocyanatodiphenylmethane
2,6-dimethyl-4,4'-diisocyanatodiphenyl
2,4-diisocyanatostilbene
3,3'-dimethoxy-4,4'-diisocyanatodiphenyl
1,4-anthracenediisocyanate
2,5-fluorenediisocyanate
1,8-naphthalene diisocyanate
2,6-diisocyanatobenzfuran
2,4,6-toluene triisocyanate
p,p',p"-triphenylmethane triisocyanate
trifunctional trimer (isocyanurate) of isophorone diisocyanate
trifunctional biuret of hexamethylene diisocyanate
trifunctional trimer (isocyanurate) of hexamethylene diisocyanate
polymeric 4,4'-diphenylmethane diisocyanate Capping of the selected diols or polyols with polyisocyanates to form the prepolymers of this invention is effected using stoichiometric amounts of reactants. The isocyanate-to-hydroxyl group ratio preferably should be between about 1.8 and about 2.2. Higher ratios may be used but are not preferred since they may lead to problems associated with excessive monomer present in the final products. The capping reaction may be by any convenient method or procedure. For example, the reaction may-be carried out at about 20° to about 150° C., under dry nitrogen, for about 2 hours to about 14 days, preferably in the absence of a catalyst. The reaction is terminated when the isocyanate concentration approaches theoretical values. The time period will be a function of the polyisocyanate used and the temperature at which the reaction is conducted.

It is preferred to avoid using an excess of polyisocyanate in preparing the prepolymer. Preferably, an isocyanate-to-hydroxyl group ratio of 2:1 (for example, one diisocyanate molecule per hydroxyl group of the polyol) is used to ensure complete end-capping of the polyol. Complete end-capping eliminates excessively high viscosity in the prepolymer by avoiding undue amounts of chain extension. However, a slight excess of isocyante, i.e., up to about ten percent, can be used.

It is characteristic of this second polymer system that the isocyanate content of the prepolymer is very low. This is achieved by employing high molecular weight polyols and by avoiding excessive quantities of isocyanate in the end-capping reaction so that free isocyanate monomers are unlikely to be present. The isocyanate concentration in the prepolymer should be about 0.1 to about 0.43 milliequivalents per gram, for prepolymers formed from diols or polyols of about 7,000 to 30,000 MW.

Notwithstanding a preference for low isocyanate content, the polymer system described herein affords a greater degree of flexibility in this regard than conventional systems. The presence of an organic solvent in preparing and handling the prepolymer protects against excessive viscosity resulting from the use of polyols of higher molecular weight or increased EO content, or from the use of insufficient quantities of isocyanate for complete end-capping of the diol or polyol. That is, the organic solvent permits the use of less than stoichiometric (2:1) quantities of the isocyanate monomer. Chain extension resulting from incomplete end-capping typically results in increased viscosity which may make handling of the prepolymer difficult or impossible. By contrast, the system of this invention tends not to be affected negatively by increased viscosity due to chain extension, or from any other cause, because the solvent serves to maintain the viscosity within a range suitable for convenient handling of the prepolymer.

The organic solvent used in preparing the prepolymer must be compatible with the reactants and with the end use desired for the hydrated polymer. Primarily, the solvent must be one in which the diol or polyol and/or prepolymer can be readily dissolved, preferably at ambient temperatures. Suitable solvents for preparing the prepolymer include acetonitrile, dimethyl formamide, dimethyl sulfoxide, tetrahydrofuran, dioxane, dichloromethane, acetone and methyl ethyl ketone, or mixtures thereof. Acetonitrile is preferred.

In one embodiment using an organic solvent, the diol or polyol itself is dissolved in the solvent and is reacted with polyisocyanate while in solution to yield the isocyanate end-capped prepolymer. This embodiment is particularly preferred where the diol or polyol is solid or crystalline at ambient temperatures, that is, for diols or polyols substantially or exclusively comprised of ethylene oxide units and for high molecular weight diols or polyols. In this manner, even crystalline diols or polyols can easily be handled without heating to their respective melting points. Even though the prepolymer formation reaction is conducted at elevated temperatures, utilizing an organic solvent to first place the diol or polyol in liquid form assures good reaction and prepolymer formation.

In another embodiment using an organic solvent, the isocyanate end-capped prepolymer first is prepared and then is dissolved in an organic solvent. This embodiment will be useful where the diol or polyol already is liquid or pasty at ambient temperatures and does not require dissolution in order to prepare the prepolymer. For example, diols or polyols of lower molecular weight or higher propylene oxide or butylene oxide content may be treated in this manner. Use of a solvent at the prepolymer stage is advantageous where increased viscosity occurs due to chain extension of incompletely end-capped diols or polyols.

It may be desired to add an antioxidation agent, preferably prior to preparation of the prepolymer. Antioxidants are not required to make or use the prepolymers or polymers of this invention. However, storage and handling properties may be enhanced by such an addition by preventing oxidative breakdown of the polymer or its precursors. Suitable antioxidants include the hindered phenolic compounds. Specific examples are IRGANOX TM (Ciba-Geigy Corp.) and SANTONOX TM (Monsanto Chemical Co.). The antioxidant may be added in amounts of about 0.01 to about 10% preferably about 0.02 to about 0.1%, based on the weight of the polyol or precursor to the prepolymer.

Modifying Compounds

The affinity matrix is prepared by first modifying the above described prepolymers. The prepolymers are modified or derivatized to add specific reactivity to the basic polymeric compound which is to be prepared. Specific functionality and reactivity can be imparted to an otherwise nonreactive, biocompatible polymer in this manner. As an example, in embodiments in which a polymerized structure is formed, the surface of the polymer may be generally nonadsorptive and nonreactive with the exception of the desired functionality inserted into the polymer by the process described here.

The prepolymer is modified by reacting it with a compound containing a first functional group which is isocyanate-reactive and a second functional group which imparts the desired specific reactivity to the modified prepolymer. The second functional group is isocyanate-non-reactive or is substantially less reactive with isocyanates than the first functional group. The isocyanate-reactive functional group is a sulfhydryl (—SH), amino (—$NH_2$), hydroxyl (—OH) or carboxyl (—COOH) group. The rate and extent of the modification reaction will depend in part on the first functional group of the modifying compound (that is, the NCO—reactive group) and in part on the relative molar quantities of the prepolymer and the modifying compound. Where the first functional group is an amino group contained in a diamine or polyamine compound or is a carboxyl group, a large molar excess of the modifying compound is used so that substantially all of the isocyanate groups of the prepolymer are modified.

In general, sulfhydryl groups react preferentially and rapidly with the isocyanate ("NCO") groups of the prepolymers, under conditions which cause formation of the thiolate ion (—$S^-$), as described below. The thiolate ion reacts with the isocyanate groups of the prepolymer to provide modified prepolymers containing —NHC(O)S— (thiourethane) linkages, even in the presence of amino, hydroxyl or carboxyl functional groups.

However, isocyanate-capped prepolymers will react substantially faster with sulfhydryl-containing compounds than with the compounds containing the other listed groups only when reacted under conditions in which the thiolate anion (—$S^-$) is formed as the active species. Conversely, under conditions where a sulfhydryl-containing compound will not readily form the thiolate reactive group, the prepolymer modification reaction will proceed very slowly and may not occur to any appreciable extent. That is, the presence of the sulfhydryl group alone is not sufficient for the modification reaction in the absence of suitable conditions to form the thiolate ion. For example, reaction of prepolymer and ethanethiol ($C_2H_5SH$) in acetonitrile solvent will not proceed in the absence of a catalyst to ionize the sulfhydryl group of ethanethiol.

The thiolate anion may be formed catalytically by the addition of an extramolecular catalyst. Suitable catalysts would include base catalysts (preferably a tertiary amine such as triethylamine or N-methyl imidazole) or reducing agents such as sodium borohydride. In certain cases, intramolecular or self-catalysis may occur to cause formation of the thiolate ion.

One example of a compound undergoing intramolecular catalysis is cysteamine, formed by treating cystamine (($NH_2CH_2CH_2)_2S_2$) with a reducing agent. Specifically, in the presence of mercaptoethanol or another reducing agent, the disulfide bond of cystamine is reduced to form cysteamine ($NH_2CH_2CH_2SH$) which contains both a free amino and a free sulfhydryl group. The amino and sulfhydryl groups of the cysteamine molecule interact to cause formation of the thiolate ion by intramolecular catalysis. The NCO groups of the prepolymer react preferentially with the thiolate group of the self-catalyzed cysteamine molecule, yielding a prepolymer modified via the thiolate so as to have a free amino group as the second functional group.

Alternatively, cystamine itself can be reacted with the prepolymer prior to reduction of the disulfide bond. In this case, the NCO groups of the prepolymer will react with the free amino groups of the cystamine molecule, the second functional group being blocked by the disulfide bond. Following cystamine modification of the prepolymer, a reducing agent such as mercaptoethanol is added to reduce the disulfide bond, creating the sulfhydryl group, which is the second functional group in this embodiment.

By contrast, reaction of NCO-capped prepolymers with compounds containing an amino group as the first functional group is relatively slower than reaction with thiolate-containing compounds, although reaction is still quite rapid. The amino-NCO reaction forms modified prepolymers containing —NHC(O)NH— (urea) linkages. Reaction rates between the prepolymer and modifying compounds containing amino groups will vary with pH. Unprotonated amines are preferred for faster reaction rates.

Where diamines or polyamines are used as the modifying compound, they should be employed in large excess quantities in order to cause modification of the prepolymer. By "large excess quantities" is meant greater than a 1:1 molar ratio of —$NH_2$ to —NCO groups, preferably greater than 2:1 and most preferably between about 2:1 and about 5:1. It should be understood that use of small amounts of primary or secondary diamines or polyamines will serve the function of crosslinking the modified prepolymer by reacting with the NCO-groups of multiple prepolymer molecules. This is taught in prior patents such as Matthews et al., described above. However, when used in large excess quantities, the diamines and polyamines do not serve the crosslinking function, since it is unlikely that any polyamine molecule will react with NCO-groups from more than one prepolymer molecule. Rather, the reaction serves to derivatize the prepolymer in the manner of this invention. Monoamines may be reacted in any desired relative quantity.

Reaction of NCO-capped prepolymers with compounds containing hydroxyl groups is slower still, forming modified prepolymers containing —NHC(O)O— (urethane) linkages. Under conditions where the hydroxyl group is maintained, reaction is quite slow. Examples include methanol, ethanol, ethylene glycol, etc. Methanol will react with the prepolymer to form a modified prepolymer having a methyl group as the second functional group. However, reaction may be very fast where the —O— (alkoxide) ion is formed. For example, methoxide or ethyl alkoxide would be suitable modifying compounds and would be reactive.

The fourth category of first functional groups useful in forming the modified prepolymers and polymers of this invention includes compounds having carboxyl (—COOH) groups. Compounds with aliphatic or aromatic carboxyl groups may be used. For example, certain amino-protected amino acids and peptides might be reacted with the prepolymer via the carboxyl group. As another example, 2,2-dithiodiethanoic acid can be used as the modifying compound. However, reaction of the prepolymer NCO groups with a carboxylic acid is very slow. The reaction rate can be accelerated by the addition of a base (e.g., triethylamine, N-methyl imidazole, etc.) to ionize the carboxyl group. The modified prepolymers will contain anhydride or amide linkages.

As with diamine- or polyamine-modifying compounds, compounds containing carboxyl groups should be employed in large excess quantities in order to modify the prepolymer. By "large excess quantities" is meant greater than a 1:1 molar ratio of —COOH to —NCO groups, preferably greater than 2:1 and most preferably between about 2:1 and about 5:1. When used in these large excess quantities, complete or substantially complete modification of the prepolymer —NCO groups occurs.

The prepolymer's original resistance to nonspecific protein binding can be maintained during the modification reaction of this invention. If this is a desired characteristic, care should be taken to select a modifying compound which itself is not susceptible to nonspecific protein binding. For example, it would be desired to use uncharged hydrophilic modifying compounds, such as ethanolamine. Modifying compounds which are susceptible to nonspecific protein binding (for example, those having highly charged groups) should be avoided if non-specific protein binding would be problematic.

Where biocompatibility is desired, the modifying compound should be nontoxic. On the other hand, it may be desired to render the polymer toxic for certain purposes and modifying compounds can be selected with that in mind. For example, prepolymers might be modified with biocidal compounds or the like.

Examples of suitable modifying compounds with which the prepolymer may be reacted according to this invention include the following:
2-aminoethanol (ethanolamine)
aminoethyl hydrogensulfate
aminoethane sulfonic acid (taurine)
4-aminosulfonyl-1-hydroxy-2-naphthoic acid
glucosamine
5-(aminosulfonyl) N-((1-ethyl-2-pyrrolidinyl) methyl)-2-methoxybenzamide
sulfamylphenyl-D-glucosylamine
4-carboxybenzene-sulfonamide
sulfanilamide
cyclic-AMP (cyclic-adenosine monophosphate)
2-aminoethyl phosphonic acid
tyrosine
tyramine
dibutylamine
L- or DL-cysteine (alpha-amino-beta-thiol propionic acid)
L- or DL-cysteine ethyl ester
L- or DL-cystine dimethyl ester
L- or DL-cystine (di(alpha-amino-beta-thiol propionic acid)
L- or DL-cysteinesulfonic acid
L- or DL-cysteic acid
cystamine (2,2-dithiobis(ethylamine))
2-mercaptoethanol
ethanethiol
glutathione
3-amino-1,2-propanediol
3-amino-1-propane sulfonic acid
3-aminophenyl boronic acid
2-amino-2-deoxy-D-galactose (galactosamine)
1-amino-1-deoxy-D-galactose
p-aminophenyl-alpha-D-glucose
p-aminophenyl-1-thio-beta-D-galactose
penicillamine.

In addition to these specific examples, compounds from the following groups may be used:
peptides with sulfhydryl groups
peptides with free amino groups
animal hormones
polysaccharides
lipids
nucleic acids
amino sugars
amino acids
amine surfactants
diamine and polyamines.

It may be desired to temporarily block the second functional group of the modifying compound in order to ensure that modification of the prepolymer takes place via the first functional group. This will allow for preparation of the desired modified prepolymer, without contamination from competing modification reactions. For example, where a modifying compound contains both amino and carboxyl groups, it may be desired to block the amino groups to allow modification via the carboxyl groups. Blocking procedures for various functional groups are well known. Following prepolymer modification, the second functional group is deblocked, again by well-known procedures.

Prepolymer Modification Reaction

The reaction between the prepolymer and the modifying compound may be conducted in a variety of ways by manipulating the order of addition as well as the environment in which the reaction is conducted (i.e., aqueous or nonaqueous). In addition, the degree of prepolymer modification may be controlled by the relative molar quantities of the components.

In one order of addition, the reaction may be commenced by adding the modifying compound to the prepolymer. Preferably, the modifying compound is used in a nonaqueous solution. This will result in relatively low levels of prepolymer modification, although the extent of modification also will be affected by the molar concentrations. It is preferred to use this order of addition where only small degrees of modification are desired. It is, for example, most preferred where the modifying compound is a diamine or polyamine or contains a carboxyl group. Moreover, this order specifically is not preferred where the modifying compound is a diamine or polyamine since crosslinking would be the predominant reaction, as described in Matthews et al., above. Rather, where diamines or polyamines are used, it is preferred to use them primarily or exclusively as modifying compounds. Similarly, this order of addition is not preferred for use with carboxyl group-containing modifying compounds, since only low levels of modification will be achieved. Extensive to complete modification is ensured by using the second, preferred, order of addition described below, and also by using large molar excesses of the modifying compound where that compound is a diamine, polyamine or contains carboxyl groups.

In the second, preferred, order of addition, the prepolymer is added to a nonaqueous solution of the modifying compound. Preferably, a large molar excess of the modifying compound is used where extensive or complete modification is desired. This order of addition is particularly preferred for use with diamines, polyamines and compounds containing carboxyl groups as the first functional group so that the modification reaction occurs prior to any significant amount of polymerization. If crosslinking or polymerization of a modified prepolymer of these classes is desired, it should be conducted via alternative chemistry.

The use of a non-aqueous environment is important in the above embodiment in order to avoid simultaneous polymerization. This embodiment is especially preferred where greater degrees of modification are desired. It is, for example, most preferred where the modifying compound is a diamine or polyamine or contains a carboxyl group. It is also preferred where the prepolymer is monofunctional alcohol-based. Moreover, greater control can be exerted to modify particular percentages of the prepolymer by controlling the molar ratios.

Solvents such as those listed above for preparation of the prepolymer may be used. In addition, solvents such as toluene, 2-propanol, methanol, ethanol, pyridine, and other solvents, preferably aprotic solvents, may be used. The solvent should be dried prior to use, for example, by drying over molecular sieves. If methanol or ethanol are used, great care should be taken to thoroughly dry the solvent and to avoid storage prior to use. The isocyanate of the prepolymer may react with water present in the solvent rather than reacting with the modifying compound. To this extent, the prepolymer will undergo polymerization rather than derivatization.

In this embodiment (prepolymer modification in a dry, nonaqueous solvent), the prepolymer and the modifying compound are contacted in the solvent under ambient conditions. The concentration of prepolymer can vary greatly, from close to zero to almost 100%, but preferably between about 5.0 to about 50.0% (wt/wt) prepolymer is used. Although it is possible to derivatize the prepolymer in an ambient atmosphere, it will be preferred to conduct the reaction under a dry, inert atmosphere, such as dry nitrogen, in order to preserve the isocyanate groups. At ambient temperatures, the derivatization reaction typically will be complete in up to about one hour. However, it is preferred to allow a longer time for this step (i.e., about 4 to 24 hours) in order to ensure that the reaction has gone to completion.

In another method of productive modification of the prepolymer takes place simultaneously with polymerization by contacting the prepolymer and modifying compound in the presence of water or another crosslinking agent. For example, an aqueous solution of the modifying compound may be used. The prepolymer becomes derivatized and also polymerized to some extent, due to the reaction of some of the isocyanate groups with the modifying compound and some with water. The degree of modification is controlled by the quantity of the modifying compound present in relation to the prepolymer, as well as the quantity of water present. Clearly, this embodiment is useful where partial modification is sought and where it is desired that the final product is a three-dimensional modified polymeric structure. This embodiment also is useful in those cases where the modifying compound is insoluble in non-aqueous solvents. The one-step modification reaction of this embodiment also may be advantageous in eliminating process operations.

The degree of modification versus polymerization can be controlled by balancing the relative molar concentrations of modifying compound, prepolymer and water. That is, the prepolymer and the modifying compound are reacted in sufficient quantities to allow for reaction of the desired portion of the isocyanate groups of the prepolymer. These adjustments are within the skill of the art. Ambient conditions may be used for the modification reaction in this embodiment. The intended end use of the modified polymer will dictate the desired extent to which the isocyanate groups of the prepolymer are derivatized by reaction with the modifying compound. Anywhere up to 100% of the isocyanate groups may be modified according to this invention.

Modification of up to about 15% to 30% of the NCO groups will yield a modified prepolymer capable of significant polymerization and subsequently, activation. Modification in the middle range, that is, greater than about 15% to 30% and less than about 50% of the prepolymer isocyanate groups, is unlikely to form a stable gel. At this extent of modification, the modified polymer or prepolymer typically will be characterized by solubility in rather than reactivity with water, although at the lower end of the modification range some gelling or foaming will occur. In general, gelling will occur only where less than about one-third of the terminal NCO groups of the prepolymer are modified.

Polymerization

As previously described, where up to about one-third of the isocyanate groups of the prepolymer are modified, polymerization may be accomplished by the addition of a stoichiometric excess of water or aqueous solution relative to the total remaining available isocyanate groups. Where the prepolymer has been modified to a greater extent, "polymerization" is somewhat of a misnomer, although the composition may be cured by final treatment of the modified prepolymer with water or an aqueous solution. In this case, the remaining isocyanate groups on the modified prepolymer are reacted with water to cure the modified composition, although little or no polymerization occurs due to the high percentage of NCO groups which have undergone reaction with the modifying compound. Any remaining NCO groups react with the water. Alternatively, the remaining NCO groups could be used to couple the modified prepolymer to a surface or to another compound.

A modified prepolymer-aqueous solution may be prepared, with or without an organic solvent, to initiate polymerization and curing. Once the solution is completely mixed, it should be left unagitated in order to allow crosslinking to occur. As polymerization begins to occur, gelling takes place. At the gelling stage, the modified polymer sets and takes on the physical form of the final cured product, forming a semisolid elastic matrix. Setting time may be on the order of from about thirty seconds to about one hour. Unreacted isocyanate groups still will be present at this stage. A gel-forming polymer mixture loses its ability to flow, becoming a jelly-like solid or semisolid mass. Alternatively, the modified prepolymer-organic solvent solution may be applied to the desired substrate and subsequently contacted with water or an aqueous solution to initiate polymerization and curing.

Preferably, water alone is used for polymerization and curing, but solutes or particulates may be present, if desired. Solutes which react with the isocyanate groups will become an integral part of the hydrogel. Care should be taken with such solutes since too high a concentration may result in excessive end-capping of the prepolymer to such an extent that polymerization will be precluded. It will generally be preferred to avoid using isocyanate-reactive compounds other than the modifying compound.

In preparing an aqueous solution containing the modified prepolymer, the modified prepolymer-to-water ratio should be about 1:1 to about 1:20, preferably about 1:5 to about 1:15. Setting time increases as the proportion of modified prepolymer in the aqueous solution decreases. The solution should be stirred or agitated until completely mixed and then allowed to stand so that a three-dimensional modified polymer structure may form.

Polymerization begins to occur spontaneously with formation of urea upon contact of the unmodified isocyanate groups with water. Catalysts or crosslinking agents are not required but are considered optional and may be used if desired. Suitable catalysts include organic tin salts (e.g., dibutyltin dilaurate) and tertiary amines. Suitable crosslinking agents include primary and secondary polyamines and polyfunctional isocyanates.

The polymer continues curing until the chemical reaction of all residual isocyanate groups with water is complete or approaches completion. Complete curing reaction may take hours, days or weeks, depending on the conditions and the polyisocyanate used, although it is essentially complete in about four to twenty-four hours. The curing time may be shortened by addition of chain terminating or inactivation agents, such as ethanolamine, which cause end-capping without chain extension. The final modified polymer product is a polyurea-urethane.

Where a hydrogel is to be formed, only setting (that is, gelation) is required to set the shape of the modified polymer. However, complete or substantially complete curing is necessary in order to produce a biocompatible hydrated polymer which resists nonspecific protein binding. Complete isocyanate reaction may be ensured by soaking the polymer in water to reduce or eliminate the availability of residual isocyanate groups, or by incorporating chain terminating agents as described above. This eliminates residual isocyanate groups which may bind proteins which come into contact with the hydrated polymer.

Setting and curing time will vary, depending in part on the concentration of prepolymer present in the solution from which the polymer is formed. Setting time decreases with higher prepolymer concentrations. In addition, setting time depends on the type of polyisocyanate used in preparing the prepolymer. Aromatic polyisocyanate end-capped prepolymers will set rapidly, usually reacting in somewhat less than one minute, although the curing time may be longer. Prepolymers capped with aliphatic polyisocyanates have a longer setting time, typically about 20 to 90 minutes, and may take from up to several hours to several weeks for complete curing. If desired, the polymer may be subjected to a drying step.

When the modified polymer of this invention is prepared as a coating in the form of a thin film or a monomolecular or substantially monomolecular layer, a distinction between setting and curing is less apparent. In this embodiment, the modified prepolymer-organic solvent solution is deposited on a substrate and excess organic solvent is removed. Atmospheric moisture may be sufficient for polymerization of the gel coating or layer. Water is added to promote chain extension and crosslinking of the modified polymer on the substrate surface. This crosslinking is necessary to stabilize the coating, which otherwise would wash off under certain conditions, such as high water flow rates, or high or low pH, for example. The coating is subjected to this water treatment for about 15 minutes to about 24 hours, or longer, to ensure complete or substantially complete reaction of the isocyanate groups. If desired, the coating may be treated with a chain terminating agent, such as ethanolamine, to ensure reaction of the residual isocyanate groups.

Organic solvents may be useful in preparing hydrated polymers (i.e., hydrogels) according to this invention. During polymerization, the presence of a solvent enables the system to tolerate higher levels of excess isocyanate (over stoichiometric amounts) without causing disruption of the hydrated polymer formation. Carbon dioxide formed by the reaction of excess isocyanate monomer and water simply effervesces due to the system's low viscosity, rather than becoming entrapped to elicit foam formation. Of course, if foams are desired, polymerization would be conducted in the absence of or with much lower levels of solvent. The solvents listed above as being suitable for use in preparing the prepolymer may also be used here. In addition, methanol, ethanol, 2-propanol and dichloromethane, or mixtures thereof, may be used.

If an organic solvent is used in the preparation of the prepolymer, modified prepolymer or modified polymer, it most frequently will be removed prior to use of the polymer. If methanol is selected, it must be removed promptly (i.e., within a few minutes to several hours) in order to avoid excessive end-capping of the isocyanate groups, which will prevent polymerization. Solvent may be removed from the modified prepolymer prior to curing or may be allowed to evaporate during the process of depositing or coating the modified prepolymer onto a desired coatable substrate or forming the modified prepolymer into the desired shape. Alternatively, where a thin polymeric coating is desired, the modified prepolymer may be adsorbed onto a substrate directly from the solvent solution after which the entire coated substrate may be removed from the solvent. In most cases where curing is accomplished in the presence of the solvent, the solvent is removed from the modified polymer after curing, either by evaporation or by washing with water. In these cases, it is necessary to use a solvent which is water soluble. The organic solvent-modified prepolymer solution then will be compatible with the aqueous solution in which the polymer will be formed, resulting in an aqueous modified prepolymer solution, not an emulsion or dispersion.

Polymer Activation

The modified polyurea-polyurethane or polyurethane polymer, depending upon the prepolymer used, will be characterized by the specific reactivity provided by the second functional group of the modifying compounds. To activate the modified polymer, the polymer is reacted with a suitable activating compound through said second functional group. This reaction serves to convert the second functional group to a reactive species capable of selectively covalently binding a ligand or binder molecule of interest.

Activation of the modified polymer may be accomplished using a wide variety of activating compounds. The term "activating compound" is used herein to designate bifunctional or polyfunctional compounds which react with said second functional group to leave residual reactive groups available for covalently coupling a desired ligand or binder molecule. Activating compounds of this type are well known in the field of affinity separation and will vary depending upon the nature of the second functional group and the ligand or binder molecule to be bound. Suitable activating compounds include, but are not limited to, p-nitrophenyl chloroformate; N-hydroxy-succinimide chloroformate; 1,1'-carbonyldiimidazole; 2,2,2-trifluorethanesulfonyl chloride; toluenesulfonyl chloride and the like. Other activating compounds include sulfosuccinimidyl 4-(N-maleimidomethyl) cyclo-hexane-1-carboxylate; pyridyl disulfide; 1-ethyl-3-(3-dimethylaminopropyl) carbodiimide; glutaraldehyde and the like. The activating agents may be homobifunctional crosslinking reagents such as homobifunctional N-hydroxysuccinimide esters or imidoesters; or heterofunctional crosslinking reagents such as N-succinimidyl 3-(2-pyridyldithio) propionate, succinimidyl 4-(N-maleimidomethyl) cyclohexane-1-carboxylate and the like. Crosslinking reagents containing photoactivated groups, such as nitrenes or carbenes, are also suitable for use as activating agents.

The degree of activation of the modified polymer will be controlled by the degree of prepolymer and polymer modification and in part on the relative molar quantities of the activating compound. Modification of up to about 15% to about 30% of the NCO groups on the prepolymer is preferred. A large molar excess of the activating compound is contacted with the polymer so that essentially all or substantially all of the second functional groups of the polymer are reacted. Preferably greater than a 1:1 molar ratio of the activating compound to polymer, most preferably about 2:1 to about 5:1 molar ratio, is used.

In general, the modified polymer, or a substrate having a thin film or a monomolecular or substantially monomolecular layer of the modified polymer thereon, is contacted with the activating compound in the presence of a solvent. The solvent may be aqueous or nonaqueous depending upon the activating compound used. Where the modified polymer is coated onto a support, care should be taken to select a solvent which will not erode or otherwise damage the substrate.

The activating compound is contacted with the modified polymer for about 2 to 17 hours, or longer, to ensure complete or substantially complete reaction of all of the second functional groups on the modified polymer. As will be obvious, reaction conditions, e.g. temperature and atmospheric conditions etc . . . , will vary depending upon the activating agent and polymer used. The solvent is thereafter removed, e.g. by filtration or evaporation, and the residue dried to provide the activated polyurethane or polyurea-polyurethane polymer matrix. The matrix can then be reacted with a bioaffinity agent in an aqueous or nonaqueous medium to covalently attach the desired agent to the support.

Affinity Matrix

The support matrices of the invention are comprised of the activated hydrated polyurea-polyurethane or polyurethane polymer, or, in the alternative, are characterized by a support coated with the activated hydrated polymer. The support may be in the form of a microporous or nonwoven membrane, particulate porous or nonporous media, or a nonporous devise such as a microtiter plate.

Microporous materials such as those now utilized for diagnostics will be suitable. Nylon membranes are frequently used. Alternatively, membranes or polypropylene, various polyesters, polyvinyl fluoride, Teflon (TM, E. I. DuPoint de Nemours & Co.) or cellulose may be used. Membranes of woven or nonwoven materials may be of suitable surface area such that the test fluid and any solutes contained therein will wet the surface and may or may not pass through the support. Membranes with pore sizes of about 0.05 or less to about 5.0 microns or greater are typically used. The membrane material must be insoluble in the solvents used both in preparing the assay support matrix and in conducting the assay itself.

Alternatively, porous or nonporous particulate supports may be used. For example, inorganic particles, e.g. silica gel, and organic particles, e.g. charcoal, polystrene and polyamine particles, would be suitable. The particle size will be chosen according to the format in which the support matrix will be used. For example, if the matrix will be in a column or packed bed configuration, the particles must be of sufficient size to allow flow of the test fluid and reagent solutions through the bed. One micron beads may be desirable for use in this embodiment. Here again, the material chosen should be insoluble in the solvents used in preparing the matrix and polymer system used in this invention.

In another alternative embodiment, the support may be a nonporous assay device, such as a microtiter plate. Devices such as this typically are composed of materials such as polystyrene, polypropylene, polyvinylchloride and the like. Care should be taken in preparing support matrices of this embodiment either to select solvents which will not compromise the integrity of the substrate, or to quickly remove the solvent after the coating step before the substrate can be eroded or otherwise damaged.

Properties of Affinity Matrix

The affinity matrices of the invention are unique and offer significant advantages over conventional affinity matrices. The affinity matrices are resistant to nonspecific protein adsorption. Only targeted proteins will be bound to the support matrix by virtue of specific binding sites provided thereon. Thus, interference from other proteins present in the environment of use will be eliminated, as will be possible ambiguity of desired results caused by indiscriminate binding of unwanted proteins.

The affinity matrix will be characterized by specific reactivity provided by the residual functional groups of the activating compound, or by unique binding sites associated with a bioaffinity agent bonded thereto. Modification of only a limited number of prepolymer groups permits the introduction of functional or reactive groups on the polymer matrix while maintaining the biocompatibility of the original prepolymer. The prepolymer's original resistance to nonspecific protein binding is also maintained in the matrix of the invention. However, selection of modifying and activating compounds which themselves are not susceptible to nonspecific protein binding may be desired to enhance the nonprotein adsorptive properties of the matrix.

Where biocompatibility is desired, the modifying and activating compounds should be nontoxic. On the other hand, it may be desired to render the polymer matrix toxic for certain purposes. Modifying and activating compounds can be selected with such purposes in mind. Biocompatibility as used herein refers to the resistance to adsorption of protein and to the lack of interactiveness with physiological surfaces, as discussed above.

Use of Affinity Matrix

The affinity matrices of this invention are suited for use in various medical and laboratory devices and procedures in which contact with blood or other protein-containing fluids, or body tissues is likely. The matrix of the invention may be used as an affinity matrix to selectively bind by covalent attachment a targeted bioaffinity agent for various commercial and research purposes. The affinity matrices may be used directly following immobilization of the bioaffinity agent without the need for a blocking step to prevent the binding of unwanted proteins.

The affinity matrix of the invention is suitable in various biomedical applications for the purification, isolation and/or quantification of a desired ligand or binder molecule. For example, silica coated with the activated polymer of the convention may be used as a chromatographic support to immobilize an antibody. The silica/activated polymer support onto which the antibody is immobilized is then used to isolate and/or purify an antigen specific from the antibody from, e.g. a crude cell extract or the extracellular fluid of a cell which produces the antigen naturally or as a result of recombinant procedures.

The affinity matrices of the invention are particularly useful in biomedical applications as extracorporeal devices for therapeutic purposes. For example, kidney dialysis patients accumulate high levels of the protein beta-2-microglobulin which deposits in the wrist joints causing severe clinical problems. The affinity matrix of the invention having an antibody to beta-2-microglobulin immobilized thereon may be used to remove the protein from the blood of patients during kidney dialysis. In a similar manner, toxic metals may be removed from the blood of patients suffering from iron overload by contacting the blood with an affinity matrix of the invention on which has been immobilized an antibody to the iron-binding protein, ferritin. In cancer therapy, chemotherapeutic agents which have been administered in toxic amounts may be removed from the blood of cancer patients using an affinity matrix of the invention having an appropriate ligand or binder molecule immobilized thereon.

The affinity matrix of the invention is ideally suitable for use in an extracorporeal therapeutic device to reduce low density lipoprotein cholesterol (hereinafter "LDL-C") levels in whole blood. In this embodiment, an affinity matrix prepared as described above, is reacted to immobilize thereon a bioaffinity agent capable of selectively removing LDL-C from the plasma components of whole blood. Suitable bioaffinity agents which may be immobilized on the affinity matrix include, but is not limited to, proteins, e.g. heparin, polyacrylic acid, dextran sulfate and antibodies specific for low density lipoproteins. The matrices of the invention facilitates the reduction of LDL-C levels in whole blood selectively without the interference from binding of unwanted proteins. The affinity matrix of the invention are also suitable for use in diagnostic assays to detect the presence of a targeted ligand or binder molecule in a test fluid. For example, a microporous membrane treated with the activated polymer system of the invention may be used to covalently bind and immobilize a bioaffinity agent for a targeted ligand or binder molecule. Test fluids and reagent solutions will be typically passed through the treated support membrane, and the presence or absence of a color change observed to determine a positive or negative result for the target ligand or binder molecule. Particulate affinity matrices prepared in accordance with the invention may also be used in a similar manner.

The examples which follow are given for illustrative purposes and are not meant to limit the invention described herein. The following abbreviations have been used throughout in describing the invention.

A—Angstrom(s)
°C.—degrees Centigrade
cm—centimeter(s)
cps—centipoise(s)
DMEM—Dulbecco's Modified Eagle's Medium
DI—deionized
F12—F12 cell culture medium
gm—gram(s)
Hg—mercury
IDPI—isophorone diisocyanate
IU—International unit(s)
M—molar
m2—square meter(s)
meq—milliequivalent(s)
mg—milligram(s)
min—minute(s)
ml—milliliter(s)
mm—millimeter(s)
mmoles—millimoles
μgm—microgram(s)
μm—micrometer(s)
μmole—micromole(s)
MW—molecular weight
N—normal
NCO—isocyanate
ngm—nanogram(s)
PBS—phosphate buffered saline
ppm—parts per million
%—percent
TM—trademark
UV—ultraviolet
v—volume
wt—weight

EXAMPLE I (Preparation of Prepolymer A)

The polyol used to prepare the prepolymers of this invention, Pluracol V7TM (BASF), a 7000 MW triol copolymer of ethylene oxide (75%) and propylene oxide (25%), was deionized and dried. Following this deionization procedure, 1687.46 gm Pluracol V7 was mixed with 165.0 gm isophorone diisocyanate (IDPI) and 0.93 gm SANTONOX RTM (Monsanto Chemical Co.) and heated at 70° C. under dry nitrogen. Isocyanate levels were determined by addition of dibutylamine and back titration with standard acid. Fourteen days were required for the isocyanate concentration to reach 0.47 meq/gm (0.39 meq/gm=theoretical). The resulting prepolymer, designated Prepolymer A, was liquid at room temperature.

EXAMPLE II (Preparation of Prepolymer B)

A prepolymer was formed by mixing 300.0 gm deionized and dried TPEG10000TM (Union Carbide Corp.) with 22.0 gm IPDI and 0.16 gm SANTONOX R. TPEG10000 is a 10,000 MW triol prepared from 100% homopolymeric ethylene oxide. The mixture was heated at 70° C. under dry nitrogen as in Example I, until isocyanate values reached 0.36 meq/gm (theoretical=0.28 meq/gm). This prepolymer, designated Prepolymer B, formed a solid when cooled to room temperature.

EXAMPLE III (Preparation of Prepolymer C)

A prepolymer was prepared by dissolving 50.0 gm (0.0125 equiv. hydroxyl) of polyethylene glycol (8000 MW) (Sigma Chemical Co.) in 100 cc (78.2 gm) acetonitrile. To this was added 3.06 gm (0.0275 equiv. isocyanate) isophorone diisocyanate and 0.03 gm SANTONOX R. The solution was heated to 70° C. under dry nitrogen in a dry, acid-washed glass flask for 14 days. The isocyanate level declined to 0.10 meq/gm at day 14 (theoretical=0.11 meq/gm). The prepolymer formed was designated Prepolymer C and was stored as a 25% solution in acetonitrile.

EXAMPLE IV (Preparation of Prepolymer D)

A prepolymer was prepared by first dissolving 50.0 gm (0.0263 equiv. hydroxyl) polyethylene glycol monomethyl ether (MW 1900) (Polysciences, Inc.) in 100 ml (79.2 gm) acetonitrile. To this solution was added 6.43 gm (0.0578 equiv. isocyanate) isophorone diisocyanate and 0.03 gm Santonox R. The solution was heated under dry nitrogen at 70° C. in an acid-washed glass flask for 8 days, at which time the isocyanate content was 0.15 meq/gm (theoretical=0.23 meq/gm). This prepolymer, designated Prepolymer D, was stored as a 42% solution in acetonitrile.

EXAMPLE V (Preparation of Prepolymer E)

A prepolymer was prepared by mixing 848.8 gm of deionized and dried polyol BASF 1123 (BASF) with 91.6 gm isophorone diisocyanate in a one liter polyethylene bottle at room temperature with mechanical stirring for 30 minutes. Dry nitrogen was purged over the mix and the bottle was sealed with a screw cap and placed in an electric oven at 85° C. After 11 days the reaction was terminated. The product had an isocyanate value of 0.43 meq/gm and a viscosity of 62,000 cps at 25° C . This prepolymer was designated Prepolymer E (low temperature). A prepolymer was prepared in the identical manner except that it was incubated in an electric oven at 125° C. for 2 days. This prepolymer was designated Prepolymer E (high temperature).

EXAMPLE VI (Preparation of Prepolymer F)

Mono-methoxy poly(ethylene glycol) with a molecular weight of 550 (160 gm, 0.291 moles) was mixed with isophorone diisocyanate (69.0 gm, 0.310 moles) in a polyethylene bottle and purged with dry nitrogen. The sample was placed in an oven and the temperature maintained at 70° C. for 20 hours. At that time, the sample was removed and the isocyanate level was determined to be 1.32 meq/gm. This product was labeled Prepolymer F.

EXAMPLE VII (Preparation of Prepolymer G)

A polyether diol was obtained comprising 84% ethylene oxide and 16% propylene oxide, with a molecular weight of 2200 (Takeda). This diol (800 gm, 0.36 moles) was mixed with IPDI (163.4 gm, 0.74 moles) and placed in a polyethylene bottle under dry nitrogen. The sample was heated at 70° C. for 10 days at which time the isocyanate level was found to be 0.75 meq/gm. The reaction was terminated at this point and the product was stirred under dry nitrogen. The product was labeled Prepolymer G.

EXAMPLE VIII (Preparation of Modified Hydrated Polymer-coated Silica Support)

In this example, 10.0 gm (0.40 meg. NCO/gm) of Prepolymer E (high temperature) was dissolved in 20 ml dry methylene chloride. To this was added an amount of ethanolamine (0.037 gm, 0.60 meq) equivalent to 15% of the isocyanate in the prepolymer. This was allowed to react for at least 1 hour before adding to the solution 20 gm of silica (Matrex TM Silica Si, Amicon Corporation, Danvers, Mass.). This silica has a particle size of 20–45 µM, and a pore size of 500Å. The suspension was shaken on an orbital shaker at room temperature for 18 hours, filtered through a 40 µM glass frit, then mixed with 200 ml water for 8 hours to cure the polymer. After filtering and washing with acetonitrile, the coated silica was dried under vacuum at 40° C. Thermal gravimetric analysis indicated a coating of 30% (w/w), thus essentially all the polymer added was deposited on the silica.

EXAMPLE IX (Preparation of Activated Hydrated Polymer-coated Silica Support)

Prepolymer E (high temperature) was partially derivatized with ethanolamine and coated onto silica essentially as described in Example VIII. The coated silica support (10.0 gm) was suspended in 40 ml acetone containing 0.8 gm pyridine and 0.8 gm p-nitrophenyl chloroformate at 4° C. for 40 minutes. The coated silica was filtered, washed and dried under vacuum. It was stored at 4° C. until used. The extent of activation was measured by treating a sample of activated support with 0.2N NaOH and measuring the absorbance of the released nitrophenol at 400 nm. By this method a value of 22 µmoles/gm was obtained which is the same as the level of hydroxyl group available for activation.

EXAMPLE X (Binding of Calf Intestinal Alkaline Phosphatase to Activated Support)

A solution of alkaline phosphatase was prepared at a concentration of 15 mg/ml in 0.1M glycine, pH 8.0 containing 1 mM $MgCl_2$ and 1 mM $ZnCl_2$. To 5.0 ml of this solution in a 15 ml screw cap tube was added 0.50 gm of activated hydrated polymer coated silica from Example IX. The suspension was rotated at room temperature for 4 hours, then at 4° C. for 17 hours. Residual unbound protein in the supernatant was quantitated using the BioRad Protein Assay Reagent. From this analysis, it was determined that the activated hydrated polymer/silica support bound 67.5 mg protein per gram of support.

EXAMPLE XI (Demonstration of Enzymatic Activity after Binding Alkaline Phosphatase to Activated Support)

A binding experiment was conducted as described in Example X, using the activated hydrated polymer/silica support as described in Example IX. In addition, a control was run in which silica coated with ethanolamine-derivatized hydrated polymer was not activated with p-nitrophenyl chloroformate. The amounts of enzyme bound to the supports were as follows:

TABLE I

| Sample # | Support | mg alkaline phosphatase bound per gm support |
|---|---|---|
| 1 | Coated silica, not activated | 0.00 |
| 2 | Coated silica, activated | 112.0 |

In a separate experiment it was demonstrated that treating uncoated, bare silica with an equivalent amount of alkaline phosphatase lead to non-specific adsorption of the enzyme to the extent of >150 mg protein per gm bare silica. As shown in Table I above, coating the silica with the hydrated polymer of the invention completely eliminated this non-specific adsorption. Further, activation of the polymer resulted in enzyme immobilization.

To determine if the enzyme bound to the support was active, 10 mg of each of the supports as described in Table I were incubated with p-nitrophenyl phosphate under standard assay conditions. The observed change in absorbance as recorded in Table II below showed that enzyme bound by the activated hydrated polymer/silica support retained enzymatic activity:

TABLE II

| Sample # | Change in absorbance at 405 nm over 20 min. |
|---|---|
| 1 | 0.027 |
| 2 | 1.73 |

EXAMPLE XII (Affinity Purification of Thrombospondin Using Modified Hydrated Polymer-coated Silica Support)

Prepolymer E (high temperature) was derivatized with ethanolamine, coated onto silica, then activated with p-nitrophenylchloroformate as described above in Example IX. To 1.0 gm of the activted support was added 2 ml of a solution of fibrinogen containing 12.5 mg/ml (25 mg total) fibrinogen in PBS (0.01M sodium phosphate, pH 7.4, 0.15M sodium chloride). After incubating 17 hours at 4° C., the supernatant was analyzed by size exclusion high pressure liquid chromatography and by difference it was found that 23.7 mg of fibrinogen bound to the support.

A blood platelet extract was centrifuged for 10 min at 10,000 $\times$g then diluted 1:2 with 20 mM Bis-Tris Propane, pH 6.0, to lower the salt concentration to 0.05M. This solution was applied to the fibrinogen support at a flow rate of 2 ml/min then washed with the same buffer until no further protein eluted. The bound protein was then reverse-eluted using 20 mM Bis-Tris Propane, pH 6.0, containing 0.5M NaCl. The protein-containing fraction which eluted from the column was found to contain 2.77 mg of thrombospondin.

The principles, preferred embodiments and modes of operation of the present invention have been described in the foregoing specification. The invention which is intended to be protected herein, however is not to be construed as limited to the particular forms disclosed, since these are to be regarded as illustrative rather than restrictive. Variations and changes may be made by those skilled in the art without departing from the spirit of the invention.

We claim:

1. An affinity matrix for chromatography and immobilization of biologically active materials comprising a support having a polyurethane coating thereon of said polymer thereon, wherein said polyurethane polymer is derived from prepolymer units of oxyethylene based alcohols having essentially all of the hydroxyl groups capped with polyisocyanate groups and having at least 15% of said polyisocyanate groups reacted with a modifying compound having a first NCO reactive group and a second functional group having a substantially less NCO reactive group, and wherein said polyurethane polymer has been activated by converting said second functional groups to an active functional group capable of covalently attaching a bioaffinity agent, said matrix being characterized by a biocompatible surface which resists nonspecific protein adsorption, wherein the modifying compound is selected from the group consisting of ethanolamine; aminoethyl hydrogensulfate; taurine; 4-aminosulfonyl-1-hydroxy-2-napththoic acid; glucosamine; 5-(aminosulfonyl) N-((1-ethyl-2-pyrrolidinyl)-methyl)-2-methoxybenzamide; sulfamylphenyl-D-glucosylamine; 4-carboxybenzene-sulfonamide; sulfanilamide; cyclic-adenosine monophosphate; 2-aminoethyl phosphonic acid; tyrosine; tyramine; dibutylamine; L- or DL-cysteine; L- or DL-cysteine ethyl ester; L- or DL-cystine dimethyl ester; L- or DL-Cystine; L- or DL-cysteinesulfonic acid; L- or DL-cysteic acid; cystamine; 2-mercaptoethanol; ethanethiol; glutathione; 3-amino-1,2-propanediol; 3-amino-1-propane sulfonic acid; 3-aminophenyl boronic acid; 2-amino-2-deoxy-D-galactose; 1-amino-1-deoxy-D-galactose; p-aminophenyl-alpha-D-glucose; p-aminophenyl-1-thio-beta-D-galactose; penicillamine; peptides with sulfhydryl groups; peptides with free amino groups; animal hormones; polysaccharides; lipids; nucleic acids; amino sugars; amino acids; amine surfactants; diamines and polyamines.

2. The matrix of claim 1 in which substantially all of said prepolymer units are oxyethylene-based diols or polyols having an average number molecular weight of about 7000 to about 30,000.

3. The matrix of claim 1 in which at least 75% of said prepolymer units are oxyethylene-based diols and polyols having an average number molecular weight of about 7000 to about 30,000.

4. The matrix of claim 2 in which said diols or polyols are capped with an aliphatic or cycloaliphatic polyisocyanate.

5. The matrix of claim 1 in which said polyisocyanate is isophorone diisocyanate or methylene bis(cyclohexyl diisocyanate).

6. The matrix of claim 1 in which up to 100% of the isocyanate groups of the prepolymer are reacted with the modifying compound.

7. The matrix of claim 1 in which the polyurethane polymer has been activated to convert essentially all of the second functional groups to an active functional group capable of covalently attaching a bioaffinity agent.

8. The matrix of claim 1 in which the polyurethane polymer has been activated to convert substantially all of the second functional groups to an active functional group capable of covalently attaching a bioaffinity agent.

9. The matrix of claim 1 in which the support is in the form of a microporous membrane or a particulate media.

10. The matrix of claim 9 in which the support is silica gel.

11. The matrix of claim 9 in which the support is charcoal.

12. The process of preparing an affinity matrix for chromatography or immobilization of biological materials, which matrix is characterized by a biocompatible surface which resists nonspecific protein adsorption, said process comprising the steps of:
   a) preparing a prepolymer, the units of which are oxyethylene-based alcohols having essentially all of the hydroxyl groups capped with polyisocyanate;
   b) reacting said polyisocyanate capped prepolymer with a modifying compound having a first functional group which is NCO reactive and a second functional group which is substantially less NCO reactive to form a modified prepolymer;
   c) coating the modified prepolymer onto a support;
   d) curing the modified prepolymer with water to form a modified polyurethane polymer characterized by the second functional group inserted in the prepolymer; and
   e) reacting the modified polyurethane polymer with an activating compound to convert the second functional group of said polymer to an active functional group capable of covalently attaching a bioaffinity agent.

13. The process of claim 12 in which a large molar excess of said activating compound is used.

14. The process of claim 13 in which essentially all of the second functional groups of the modified polyurethane polymer is converted to an active functional group capable of covalently attaching a ligand or binder molecule.

15. The process of claim 13 in which substantially all of the second functional groups of the modified polyurethane polymer is converted to an active functional group capable of covalently attaching a ligand or binder molecule.

16. The process of claim 13 in which the modified polyurethane polymer is reacted with the activating compound in a nonaqueous environment.

17. The process of claim 13 in which the prepolymer is coated onto a support prior to curing with water.

18. The process of claim 13 in which the prepolymer units are oxyethylene based diols and polyols which are capped with an aliphatic polyisocyanate.

19. The process of claim 13 in which about 15% to about 30% of the prepolymer isocyanate groups are modified.

20. The process of claim 13 in which the prepolymer is coated onto a silica or charcoal prior to curing with water.

21. An affinity chromatographic device comprised of the matrix of claim 1.

22. An immobilized bioaffinity agent comprising a bioaffinity agent covalently attached to the matrix of claim 1.

23. An extracorporeal therapeutic device comprised of the immobilized bioaffinity agent of claim 22.

24. A purification or isolation system for a biologically-active ligand or binder molecule, said system comprising the immobilized bioaffinity agent of claim 22, wherein the bioaffinity agent is capable of selectively binding said ligand or binder molecule.

25. A diagnostic assay system comprising the affinity matrix of claim 1 having a bioaffinity agent covalently attached thereto, and further comprising a holder for said matrix.

* * * * *